United States Patent
Moss et al.

(10) Patent No.: US 10,758,476 B1
(45) Date of Patent: Sep. 1, 2020

(54) DEODORANT WITH SWEAT-ACTIVATED TECHNOLOGY

(71) Applicant: Type A Brands, LLC, Santa Monica, CA (US)

(72) Inventors: Allison R. Moss, Santa Monica, CA (US); Christopher R. Stahl, Pioneertown, CA (US)

(73) Assignee: TYPE A BRANDS, LLC, Santa Monica, CA (US)

( * ) Notice: Subject to any disclaimer, the term of this patent is extended or adjusted under 35 U.S.C. 154(b) by 0 days.

(21) Appl. No.: 16/134,866

(22) Filed: Sep. 18, 2018

Related U.S. Application Data

(60) Provisional application No. 62/559,980, filed on Sep. 18, 2017.

(51) Int. Cl.

| | |
|---|---|
| *A61K 8/9794* | (2017.01) |
| *A61Q 15/00* | (2006.01) |
| *A61K 8/37* | (2006.01) |
| *A61K 8/891* | (2006.01) |
| *A61K 8/92* | (2006.01) |
| *A61K 8/19* | (2006.01) |
| *A61K 8/365* | (2006.01) |
| *A61K 8/73* | (2006.01) |
| *A61K 8/34* | (2006.01) |

(52) U.S. Cl.
CPC ............. *A61K 8/9794* (2017.08); *A61K 8/19* (2013.01); *A61K 8/34* (2013.01); *A61K 8/365* (2013.01); *A61K 8/37* (2013.01); *A61K 8/375* (2013.01); *A61K 8/732* (2013.01); *A61K 8/891* (2013.01); *A61K 8/922* (2013.01); *A61K 8/927* (2013.01); *A61Q 15/00* (2013.01); *A61K 2800/30* (2013.01)

(58) Field of Classification Search
CPC .......... A61K 8/9794; A61K 8/19; A61K 8/34; A61K 8/365; A61K 8/37; A61K 8/375; A61K 8/732; A61K 8/891; A61K 8/922; A61K 8/927; A61K 2800/30; A61Q 15/00
See application file for complete search history.

(56) References Cited

U.S. PATENT DOCUMENTS

| | | | |
|---|---|---|---|
| 5,711,941 A | 1/1998 | Behan | |
| 8,992,898 B2 | 3/2015 | Klingman | |
| 9,566,223 B2 | 2/2017 | Klingman | |
| 9,668,948 B2 | 6/2017 | Klingman | |
| 2003/0224063 A1* | 12/2003 | Brooks | A61K 8/11 424/657 |
| 2006/0141014 A1 | 6/2006 | Eknonian | |
| 2007/0299410 A1 | 12/2007 | Eknonian | |
| 2008/0317795 A1 | 12/2008 | Traynor | |
| 2011/0104091 A1 | 5/2011 | Maitra | |
| 2012/0100095 A1* | 4/2012 | Ayala | A01N 59/16 424/76.8 |
| 2012/0107261 A1 | 5/2012 | Banowski | |
| 2013/0149397 A1 | 6/2013 | Chen | |
| 2015/0164768 A1* | 6/2015 | Novack | A61K 8/73 424/401 |
| 2015/0290111 A1 | 10/2015 | Fan | |
| 2015/0359742 A1 | 12/2015 | Fassih | |
| 2016/0136080 A1 | 5/2016 | Sengupta | |
| 2016/0303037 A1 | 10/2016 | Joshi | |

FOREIGN PATENT DOCUMENTS

| | | |
|---|---|---|
| DE | 102011083872 | 6/2012 |
| EP | 2442780 B1 | 4/2012 |
| WO | WO1998055088 A1 | 12/1998 |
| WO | WO2010009976 A2 | 1/2010 |
| WO | WO2010009979 A1 | 1/2010 |
| WO | WO2010145919 A2 | 12/2010 |
| WO | WO2010145921 A2 | 12/2010 |
| WO | WO2016062521 A1 | 4/2016 |
| WO | WO2016142329 A1 | 9/2016 |

OTHER PUBLICATIONS

Speed Stick 24/7 Anti-Perspirant Deodorant Stick—Icy Surge; Cool Fusion; Fresh Rush; 24/7 Anti-Perspirant Deodorant Gel—Icy Surge; Cool Fusion; Fresh Rush Manufacturer: Colgate-Palmolive Co. Category: 308—Deodorants &Anti-Perspirants; Product Alert 31.23 (Dec. 9, 2002), Marketing Intelligence Services Ltd., United States.
Blumenthal, Consumer's World; A Deodorant Aimed at the Fitness Set, New York Times, Late Edition (East Coast) [New York, N.Y] Feb. 24, 1990: 1.50.

\* cited by examiner

*Primary Examiner* — Blessing M Fubara
(74) *Attorney, Agent, or Firm* — Keith G. Haddaway; Venable LLP; Miguel A. Lopez

(57) ABSTRACT

A glycerin-in-oil deodorant composition is disclosed that contains a continuous phase comprising one or more oils, silicones, esters and/or waxes; a discontinuous phase comprising glycerin and water; an antimicrobial agent; a moisture-absorption agent; an odor neutralizing agent; and an emulsifier.

20 Claims, No Drawings

DEODORANT WITH SWEAT-ACTIVATED TECHNOLOGY

RELATED APPLICATIONS

This application claims priority to U.S. Provisional Patent Application No. 62/559,980, filed Sep. 18, 2017, the contents of which are incorporated herein by reference in their entirety.

BACKGROUND

The invention relates to a glycerin-in-oil deodorant composition and methods of use. In particular, the invention relates to a glycerin-in-oil deodorant composition having a continuous phase having one or more oils, silicones, esters and/or waxes, a discontinuous phase having glycerin and water, an antimicrobial agent, a moisture-absorption agent, an odor neutralizing agent and an emulsifier.

Currently available solutions to combat or prevent underarm sweating, body odor and wetness have possible health risks and/or do not work very well. Mainstream deodorant and antiperspirant products often contain ingredients that are known to be or thought to be harmful to our health, and they do not always provide lasting odor and/or wetness protection.

Alternative deodorant products on the market categorized as "natural deodorants" tend to promote having safe or naturally-based ingredients. However, such products tend to lack in efficacy and are often an unpleasant (sticky, messy, smelly, complicated) user experience.

Accordingly, there remains a need for safe and effective deodorant compositions.

SUMMARY

An embodiment of the current invention relates to a glycerin-in-oil deodorant composition having a continuous phase having one or more oils, silicones, esters and/or waxes; a discontinuous phase having glycerin and water; an antimicrobial agent; a moisture-absorption agent; an odor neutralizing agent; and an emulsifier.

An embodiment of the current invention relates to a glycerin-in-oil deodorant composition having a continuous phase having one or more oils, silicones, esters and/or waxes; a discontinuous phase having glycerin and water; an antimicrobial agent having zinc citrate, silver chloride, and triethyl citrate; an odor neutralizing agent having sodium bicarbonate; a moisture-absorption agent having a hydrophilic starch; and an emulsifier. In such an embodiment, the sodium bicarbonate is present in the continuous phase and in the discontinuous phase.

An embodiment of the current invention relates to a glycerin-in-oil deodorant composition having a continuous phase having one or more oil, silicone or wax, wherein the oil, silicone, and/or wax together are from about 35% to about 75% by weight of the entire composition; a discontinuous phase having glycerin and water, wherein the glycerin is present in an amount of from about 5% to about 25% by weight of the entire composition and the water is present in an amount of from about 0.1% to about 2% by weight of the entire composition; an antimicrobial agent in an amount of from about 1% to about 11% by weight of the entire composition; a moisture-absorption agent in an amount of from about 1% to about 30% by weight of the entire composition; an odor neutralizing agent in an amount of from about 0.1% to about 20% by weight of the entire composition; and an emulsifier in an amount of from about 1% to about 16% by weight of the entire composition.

An embodiment of the current invention relates to a glycerin-in-oil deodorant composition having a continuous phase comprising one or more oil, silicone or wax, where the oil, silicone, and/or wax together make up from about 50% to about 60% by weight of the entire composition; a discontinuous phase comprising glycerin and water, wherein the glycerin is present in an amount of from about 10% to about 15% by weight of the entire composition and the water is present in an amount of from about 0.2% to about 1% by weight of the entire composition; an antimicrobial agent in an amount of from about 3% to about 8% by weight of the entire composition; a moisture-absorption agent in an amount of from about 3% to about 18% by weight of the entire composition; an odor neutralizing agent in an amount of from about 3% to about 9% by weight of the entire composition; and an emulsifier in an amount of from about 7% to about 11% by weight of the entire composition.

An embodiment of the current invention relates to a method for treating perspiration in a subject including contacting a skin surface region of the subject with any one of the compositions described above.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

As used throughout this description, the term "subject" refers to a mammal. In some cases, the mammal is human.

As used throughout this description, the term "perspiration" refers to the process of sweating and to the moisture and/or odor related to sweating.

As used throughout this description, the phrase an "effective amount" of a composition of the invention is measured by the effectiveness of a compound of the invention to alleviate moisture and/or odor caused by perspiration and/or prevent or limit antimicrobial growth in and/or around an area of application.

As used herein and unless otherwise indicated, the term "formulation" refers to a composition comprising one or more of the compounds described below in an emulsion to be used as a deodorant a particular dosage such as a solid, a cream, a liquid or an aerosolized form.

As used herein and unless otherwise dictated by context, the use of "a" and "an" agent does not preclude the use of more than a single agent. For example, "an antimicrobial agent" does not preclude its being "one or more antimicrobial agents."

As used herein the term "free of" a particular compound implies the lack of detectable amount that particular compound, or where the particular compound is not intentionally added to the composition.

As used herein the term "essentially free of" a particular compound refers to either complete exclusion (i.e., the lack of addition) of the particular compound or agent from a composition or formulation, or the presence of the particular compounds or agent in a concentration below the minimal concentration required for minimal activity of the compound or agent. By way of non-limiting example, when applied to aluminum salts and zirconium salts, a composition or formulation that is essentially free of these agents would include a composition or formulation wherein the concentration of the aluminum salt and/or zirconium salt is either non-existent, or lower than the minimal concentration required for use in an antiperspirant. Such a minimum concentration would be understood to be at or less than about 5-10% by weight, for example. In preferred embodiments, a minimum concentration is less than about 5% by weight and more preferably less than about 1% by weight.

As used herein, the terms "aluminum salts" and "zirconium salts" refer to aluminum or zirconium salts generally approved and used as active ingredients in antiperspirants. Non-limiting examples of aluminum salts and zirconium salts include Aluminum chloride, Aluminum chlorohydrate, Aluminum chlorohydrex polyethylene glycol, Aluminum chlorohydrex propylene glycol, Aluminum dichlorohydrate, Aluminum dichlorohydrex polyethylene glycol, Aluminum dichlorohydrex propylene glycol, Aluminum sesquichlorohydrate, Aluminum sesquichlorohydrex polyethylene glycol, Aluminum sesquichlorohydrex propylene glycol, Aluminum zirconium octachlorohydrate, Aluminum zirconium octachlorohydrex, Aluminum zirconium pentachlorohydrate, Aluminum zirconium pentachlorohydrex, Aluminum zirconium tetrachlorohydrate, Aluminum zirconium tetrachlorohydrex, Aluminum zirconium trichlorohydrate, Aluminum zirconium trichlorohydrex, and Aluminum hydrochloride. These terms do not refer to aluminum and zirconium that are covalently bound or complexed in other compounds. In particular, aluminum silicates naturally associated with certain formulations or compositions such as zeolite are not considered to be terms "aluminum salts" or "zirconium salts".

As used herein, "anti-microbial" and "anti-bacterial" are used interchangeably to refer to a component or combination of components that reduces, retards, or eliminates the growth of bacteria and other microbes. In particular, "anti-microbial" and "anti-bacterial" are used refer to a component or combination of components that reduces, retards, or eliminates the growth of odor causing bacteria and other microbes.

At times, the invention or its components are described in terms of a particular function or theory of operation. The invention is not limited to or restricted by the theory of operation, but this is intended to be a guide to the scope of the invention and its components. Where the function of a component is specified, it refers to what is believed to be the primary function; however, particular components may serve multiple functions in varying degrees.

In addition to the aforementioned ingredients, compositions of the invention may further include one or more accessory ingredient(s) selected from encapsulants, diluents, buffers, flavoring agents, binders, disintegrants, surface active agents, thickeners, lubricants, preservatives (including antioxidants), and the like.

Some embodiments of the invention relate to a new form of safe, non-toxic, healthy deodorant that protects against body odor and wetness for long periods of time. It works all day and all night, and it can work up to 48 hours. The individual ingredients are all safe and non-toxic. In preferred embodiments, many ingredients are of natural origin or naturally-derived, rather than being synthetic, i.e., created entirely in a lab. The safety of the formula has been validated by a third-party expert.

Some embodiments of the invention relate to a deodorant composition comprising a glycerin in oil emulsion. This emulsion is unique amongst deodorants on the market today. The emulsion allows the deodorant to work when activated by wetness, i.e., sweat. This allows the formula to last over long periods of time, mimicking a time release type of effect. More specifically, the glycerin phase acts to collect and/or absorb sweat, thereby attracting moisture and allowing for a time release of active agents contained within the glycerin to prevent or neutralize odor. In some embodiments, the composition itself is formulated such that the active agents are released gradually over a period of time, as opposed to all at once. In some embodiments, the composition itself is formulated such that the active agents are released as the composition absorbs moisture. This activity improves and extends the deodorant's performance in odor control and wetness absorption as compared to other types of formulations on the market. In addition, the oil phase creates a superior texture and aesthetic result—the formula is soft, smooth, lightweight, goes on sheer, and feels dry to the touch when applied under the arms, unlike current products on the market.

In some embodiments, the formula incorporates several "active" ingredients that work together to prevent or neutralize odor and absorb perspiration as identified further below. Such ingredients include Baking Soda, Arrowroot Powder, Cornstarch, Coconut Oil, Aloe Vera extract. It also includes ingredients not typically found in other natural deodorant formulas such as: Triethyl Citrate, Zeolite, Zinc Citrate, and Silver Chloride.

Embodiments of the invention have superior performance over competing products in terms of eliminating odor and absorbing wetness. Embodiments also offer an improved user experience.

Some embodiments of the invention are activated by the user's sweat and can continue to be activated over long periods of time (24 or even 48 hours) without diminished results in odor and wetness protection.

Some embodiments of the invention include several anti-bacterials (Zinc Citrate, Silver Chloride, Triethyl Citrate), baking soda, starches, and zeolites to eliminate odor and absorb wetness. Such embodiments offer better results in terms of continuous odor protection and wetness absorption than most other formulas on the market and are not gritty, wet, sticky, goopy or irritating upon application and remain comfortable throughout the day.

An embodiment of the invention relates to a glycerin-in-oil deodorant composition having a continuous phase comprising one or more oils, silicones, esters and/or waxes; a discontinuous phase comprising glycerin and water; at least one antimicrobial agent; at least one moisture-absorption agent; at least one odor neutralizing agent; and at least one emulsifier.

Some embodiments include one or more esters, waxes and oils selected from any of the following ingredients and/or alternatives: Helianthus Annuus Oil, Rosehip Seed Oil, Theobroma Cacao (Cocoa) Seed Butter, Castor (Ricinus communis) Oil, Caprylic/Capric Triglyceride (fractionated coconut oil), Olea Europaea (Extra Virgin Olive Oil), Prunus Armeniacae (Apricot), Kernel Oil, Shea Butter, Sustainable (Butyrospermum parkii) Safflower Oil (Carthamus tinctorius), Cocoa Butter (Theobroma cacao), Palm Oil (Elaecis oleifera), Sweet Almond Oil (Prunus amygdalus dulcis), Jojoba Oil (Simmondsia chinensis), Avocado Oil (Persea Americana), Callophyllum inophyllum (tamanu) oil Euphorbia Cerifera (candelilla) Wax, Candela Wax, Calendula Officinalis Flower Extract, diisoppropyl adipate, dicaprylyl carbonate.

Embodiments of the invention include one or more anti-microbial compounds. Such compounds reduce, retard, or eliminate the growth of bacteria and other microbes. In particular, such compounds reduce, retard, or eliminate the growth of odor causing bacteria and other microbes. In some embodiments, the one or more anti-microbial compounds are selected from the list consisting of zinc citrate, silver chloride, triethyl citrate, witch hazel extract, anti-microbial essential oils, zinc ricinoleate, anti-microbial zinc salts, zeolite and O-Cymen-5-ol. More preferably, in some embodiments, the one or more anti-microbial compounds are selected from the list consisting of zinc citrate, silver chloride and triethyl citrate. In some embodiments the antimicrobial agent is in an amount of from about 1% to about 11% by weight of the entire composition, or preferably about 3% to about 8% by weight of the entire composition.

Embodiments of the invention include one or more odor neutralizing compounds. Such compounds reduce, eliminate, neutralize or mask odors associated with perspiration. In some embodiments, the one or more odor neutralizing compounds are selected from the list consisting of sodium bicarbonate, magnesium hydroxide, magnesium sulfate, zeolite, and citronella. More preferably, in some embodiments, the one or more odor neutralizing compound is sodium bicarbonate. In some embodiments, the odor neutralizing agent is in an amount of from about 0.1% to about 20% by weight of the entire composition, or more preferably in an amount of from about 3% to about 9% by weight of the entire composition.

Embodiments of the invention include one or more moisture absorbing agents. Such compounds reduce, eliminate, absorb or otherwise alleviate moisture associated with perspiration. In some embodiments, the one or more moisture-absorption agent is selected from the group consisting of corn starch, tapioca starch, arrowroot powder, potato starch, rice starch, silicone powder, clays (for example Fuller's earth clay, white clay, kaolin clay), silver ear mushroom extract, hyaluronic acid, squalene, bamboo extract, other wood fiber extracts, zinc oxide, and zeolite. More preferably, in some embodiments, the one or more moisture-absorption agent is a hydrophilic starch. In some embodiments, the moisture-absorbing agent is in an amount of from about 0.1% to about 30% by weight of the entire composition.

Embodiments of the invention include one or more emulsifiers. Such compounds stabilize the composition. In some embodiments, the emulsifier is selected from the group consisting of Sorbitan isostearate, Glyceryl oleate, Sorbitan oleate, Glyceryl laurate, Glycol stearate, Polyglyceryl-4 isostearate, Polyglyceryl oleate, Polyglyceryl-2 sesquiisostearate, Polyglyceryl-2 diisostearate, Glyceryl caprylate, Glyceryl undecylenate, Polygyceryl-3 Caprate, Steareth-2, Oleth-2, Lauryl PEG/PPG-18/18 Dimethicone, Bis-PEG/PPG-14/14 Dimethicone, Lauryl PEG-9 Polydimethylsiloxyethyl Dimethicone, Cetearyl olivate, Sorbitan olivate, Brassica glycerides, Xylityl Caprate/Caprylate. More preferably, in some embodiments, the emulsifier includes sorbitan oleate, glyceryl stearate, and combinations thereof. In some embodiments, the emulsifier is present in an amount of from about 1% to about 16% by weight of the entire composition, preferably from about 7% to about 11% by weight of the entire composition.

An embodiment of the current invention relates to a glycerin-in-oil deodorant composition having a continuous phase having one or more oils, silicones, esters and/or waxes; a discontinuous phase having glycerin and water; an antimicrobial agent that includes zinc citrate, silver chloride, and triethyl citrate; an odor neutralizing agent comprising sodium bicarbonate; a moisture-absorption agent that includes one or more hydrophilic starches; and an emulsifier. In such an embodiment, the sodium bicarbonate can be present in the continuous phase and in the discontinuous phase.

An embodiment of the current invention relates to the glycerin-in-oil deodorant composition of above, the continuous phase having one or more of an oil, a silicone, heptyl undecylenate, and a wax or ester.

An embodiment of the current invention relates to the glycerin-in-oil deodorant composition of above, where components of the continuous phase, e.g. a combination of silicone, heptyl undecylenate, and/or wax or ester, together make up from about 35% to about 75% by weight of the entire composition.

An embodiment of the current invention relates to the glycerin-in-oil deodorant composition above, where the oil, silicone, heptyl undecylenate, and/or wax or ester together from about 50% to about 60% by weight of the entire composition.

An embodiment of the current invention relates to the glycerin-in-oil deodorant composition above, where the glycerin makes up from about 5% to about 25% by weight of the entire composition, preferably between about 10% to about 15% by weight of the entire composition.

An embodiment of the current invention relates to the glycerin-in-oil deodorant composition above, where the water makes up from about 0.1% to about 2% by weight of the entire composition, preferably between about 0.2% to about 1% by weight of the entire composition.

An embodiment of the current invention relates to a glycerin-in-oil deodorant composition having a continuous phase comprising one or more oil, silicone, ester or wax, where the oil, silicone, ester, and/or wax together comprise from about 35% to about 75% by weight of the entire composition; a discontinuous phase comprising glycerin and water, where the glycerin is present in an amount of from about 5% to about 25% by weight of the entire composition and the water is present in an amount of from about 0.1% to about 2% by weight of the entire composition; an antimicrobial agent in an amount of from about 1% to about 11% by weight of the entire composition; a moisture-absorption agent in an amount of from about 1% to about 30% by weight of the entire composition; an odor neutralizing agent in an amount of from about 0.1% to about 20% by weight of the entire composition; and an emulsifier in an amount of from about 1% to about 16% by weight of the entire composition.

An embodiment of the current invention relates to a glycerin-in-oil deodorant composition having a continuous phase comprising one or more oil, silicone, wax or ester, where the oil, silicone, ester and/or wax together make up from about 50% to about 60% by weight of the entire composition; a discontinuous phase comprising glycerin and water, where the glycerin is present in an amount of from about 10% to about 15% by weight of the entire composition and the water is present in an amount of from about 0.2% to about 1% by weight of the entire composition; and antimicrobial agent in an amount of from about 3% to about 8% by weight of the entire composition; a moisture-absorption agent in an amount of from about 3% to about 18% by weight of the entire composition; an odor neutralizing agent in an amount of from about 3% to about 9% by weight of the entire composition; and an emulsifier in an amount of from about 7% to about 11% by weight of the entire composition.

An embodiment of the current invention relates to the glycerin-in-oil deodorant composition above, where the antimicrobial agent is selected from the list consisting of zinc citrate, silver chloride, triethyl citrate, witch hazel extract, anti-microbial essential oils, zinc ricinoleate, antimicrobial zinc salts, and O-Cymen-5-ol.

An embodiment of the current invention relates to the glycerin-in-oil deodorant composition above, where the antimicrobial agent comprises zinc citrate, silver chloride, and triethyl citrate.

An embodiment of the current invention relates to the glycerin-in-oil deodorant composition above, where the zinc citrate makes up from about 0.0001% to about 2% by weight of the entire composition, the silver chloride makes up from about 0.0001% to about 0.1% by weight of the entire composition, and the triethyl citrate makes up from about 1% to about 10% by weight of the entire composition.

An embodiment of the current invention relates to the glycerin-in-oil deodorant composition above, where the odor neutralizing agent is at least one of sodium bicarbonate, magnesium hydroxide, magnesium sulfate, zeolite, and citronella. In some embodiments, the odor neutralizing agent can be a starch. Preferred to starches for use as odor neutralizing agents are hydrophobic starches or starches modified to be hydrophobic.

An embodiment of the current invention relates to the glycerin-in-oil deodorant composition above, where the odor neutralizing agent is present in the continuous phase and/or the discontinuous phase. In exemplary embodiments, the odor neutralizing agent is present in both the continuous phase and the discontinuous phase.

An embodiment of the current invention relates to the glycerin-in-oil deodorant composition above, where the odor-neutralizing agent includes sodium bicarbonate.

An embodiment of the current invention relates to the glycerin-in-oil deodorant composition above, wherein the sodium bicarbonate makes up from about 0.1% to about 20% by weight of the entire composition, preferably from about 3.5% to about 10% by weight of the entire composition.

An embodiment of the current invention relates to the glycerin-in-oil deodorant composition above, where the moisture-absorption agent is a starch. Preferred to starches for use as moisture-absorption agent are hydrophilic starches or starches modified to be hydrophilic. In some embodiments, the current invention relates to the glycerin-in-oil deodorant composition above, where the moisture-absorption agent is selected from the group consisting of corn starch, tapioca starch, arrowroot powder, potato starch, rice starch, silicone powder, clay, silver ear mushroom extract, hyaluronic acid, squalene, zinc oxide, and silver. In some embodiments, a starch can act as both a moisture-absorption agent and an odor neutralizing agent.

An embodiment of the current invention relates to the glycerin-in-oil deodorant composition above, where the moisture-absorption agent is a hydrophilic starch.

An embodiment of the current invention relates to the glycerin-in-oil deodorant composition above, where the hydrophilic starch comprises from about 0.1% to about 10% by weight of the entire composition.

An embodiment of the current invention relates to the glycerin-in-oil deodorant composition above, where the hydrophilic starch is one or more of arrowroot, tapioca, and corn starch.

An embodiment of the current invention relates to the glycerin-in-oil deodorant composition above, where the emulsifier has a hydrophilic-lipophilic balance of between 1 and 8.

An embodiment of the current invention relates to the glycerin-in-oil deodorant composition above, where the emulsifier is present in an amount of from about 1% to about 16% by weight of the entire composition, preferably from about 7% to about 11% by weight of the entire composition.

An embodiment of the current invention relates to the glycerin-in-oil deodorant composition above, where the emulsifier is one or more of sorbitan oleate and glyceryl stearate.

An embodiment of the current invention relates to the glycerin-in-oil deodorant composition above, having one or more of diidopropyl adipate, dimethicone, heptyl undecylenate, coconut oil, bisabolol, bees wax, carnauba wax, tapioca starch, maranta arundinacea root powder, a zeolite, corn starch, aloe vera gel, and titanium dioxide.

An embodiment of the current invention relates to the glycerin-in-oil deodorant composition above, where the composition is in a cream form, a liquid form, a sprayable form, an aerosolizable form or a solid form.

An embodiment of the current invention relates to the glycerin-in-oil deodorant composition above, where the composition is essentially free of aluminum salts and zirconium salts.

An embodiment of the current invention relates to the glycerin-in-oil deodorant composition above, where the composition is free of aluminum salts and zirconium salts.

An embodiment of the current invention relates to a method for treating perspiration in a subject including contacting a skin surface region of the subject with any one of the compositions described above. Treating perspiration can include reducing, eliminating or protecting against odor caused by perspiration, wetness caused by perspiration (for example by absorbing moisture), or both. In particular embodiments, the composition eliminates, reduces or protects against both odor and wetness. It is believed that the formulation works by protecting against odor that results from the perspiration interacting with bacteria on the skin.

In a method of treating perspiration, a deodorant composition according to the invention is applied to the skin, for example under the arm. Depending on the form of the formulation, the composition may be applied by wiping, spraying, wetting, swiping, rolling or any other suitable means. The formulation can also be applied to or incorporated into a secondary item for application. For example a liquid formulation can be applied to a fabric (or wipe), and the fabic wiped on the skin to transfer the composition onto the skin. Persons of ordinary skill in the art would be well aware of other methods of applying the composition.

An embodiment of the current invention relates to the glycerin-in-oil deodorant composition above, where the composition includes one or more of glycerin, water, zinc citrate, silver chloride, triethyl citrate, arrowroot, corn starch, and sodium bicarbonate.

In some embodiments, forming a glycerin in oil emulsion allows the product to have creamier texture instead of thick wax and oil based natural deodorant that are currently marketed, as well as allows this product to have superior odor protection and wetness absorption properties. The invention expands dispensing and application possibilities, improves aesthetics and performance. Therefore, in some embodiments, glycerin is a key ingredient for the unique combination.

In some embodiments, a low level of water is important for providing a reservoir for the Silver and Zinc ions. Other competitive oil-based formulas do not contain water.

In some embodiments, the combination of several antibacterial ingredients not found in another formula on the market: zinc citrate, silver chloride, triethyl citrate.

In some embodiments, the existence of zeolite for moisture absorption in addition to the starches is unique. Various starches are found in other natural formulas, but not Zeolite. It was unexpectedly discovered that zeolite plus this combination of primarily arrowroot, with some corn starch was the most effective in wetness absorption, helping users feel dry and affording odor protection.

In some embodiments, sodium bicarbonate creates a lasting odor protection—Sodium Bicarbonate is present in both the lipid and glycerin phases at a level that maximizes efficacy (6.5%) and minimizes the irritation that Sodium Bicarbonate usually has on the skin. Irritation is a problem common to existing products that use sodium bicarbonate as an odor neutralizing agent, but is unexpectedly absent from the instant embodiments. The formula allows for those with sensitive skin to still use the product without irritation. In a recent product trial, of the 63 users who tried the product, at least 8 had sensitive skin and had no issues with irritation.

Some embodiments include one or more water soluble inorganic salt(s) selected from any of the following ingredients and/or alternatives: Sodium chloride, Calcium chloride, Magnesium sulfate, and Magnesium Hydroxide.

Some embodiments include one or more starches selected from any of the following ingredients and/or alternatives: Quinoa starch, Rice starch, Oat starch Potato Starch.

Some embodiments include one or more inorganic salt(s) with marginal water solubility selected from any of the following ingredients and/or alternatives: Silver Carbonate, Zinc Carbonate, Silver Citrate, and Zinc Lactate.

Some embodiments can also comprise a fragrance. A suitable fragrance can be added in an amount up to about 5%, for example, from about 0.001% by weight to about 5% by weight. In exemplary embodiments, the fragrance can be added in an amount up to about 4%, for example, from about 0.001% by weight to about 4% by weight, or up to about 2%, for example, from about 0.001% by weight to about 2% by weight. Preferably, fragrances are natural or naturally derived. Fragrances can consist of a single compound or component or a mixture of compounds or components. Exemplary fragrance components include, for example, Triethyl Citrate, Pogostemon Cablin Leaf Extract, Vanillin, Cistus Ladaniferus Leaf/Stem Extract, Eucalyptus Globulus Leaf, Oil Dipteryx Odorata Seed Extract, Mentha Piperita (Peppermint) Oil, Pelargonium Graveolens (Geranium) Oil, *Pinus* (spp.) sylvestris, palustra, Citrus Aurantium Dulcis (Orange) Peel Oil, Pogostemon Cablin (Patchouli) Oil, Abies Sibirica (Fir Needle) Oil, Ferula Galbaniflua (Galbanum) Resin Oil, Mentha Piperita (Peppermint) Oil, Citrus Aurantium Bergamia (Bergamot) Fruit Oil, Citrus Aurantifolia (Lime) Peel Oil, Citrus Nobilis (Mandarin Orange) Peel Oil, Citrus Limon (Lemon) Peel Oil, Citrus paradisi Citrus Nobilis Peel Oil Expressed, Linalool, Lavandula Angustifolia (Lavender) Oil, Pelargonium Graveolens Flower Oil, Elettaria Cardamomum Seed Oil, Dimethyl Heptenal. And combinations thereof.

Some embodiments specifically exclude one or more of the following ingredients: arabens, phthalates, Aluminum, sulfates, synthetic colorants or dyes, animal content (with the exception of animal derived compounds such as bees wax), formaldehyde, diethanolamine, triethanolamine, DMDM hydantoin, diazolidinyl urea, imidazolidinyl urea, quantumium 15, tetrasodium EDTA.

Embodiments of the invention are exemplified by the following non-limiting examples.

EXAMPLES

Example 1

An example embodiment of the invention is an unfragranced formulation including the following ingredients: Diisopropyl Adipate, Glycerin, Beeswax, Dimethicone, Heptyl Undecylenate, Sodium Bicarbonate, Maranta Arundinacea Root Powder, Sorbitan Oleate, Corn Starch, Copernica Cerifera (Carnauba) Wax, Triethyl Citrate, Glyceryl Stearate, Cocos Nucifera (Coconut) Oil, Zeolite, Bisabolol, Water, Aloe Barbadensis (Aloe Vera) Leaf Extract, Zinc Citrate, Silver Chloride, Titanium Dioxide.

Example 2

An exemplary embodiment of the invention is a deodorant formulation with the compositional characteristics identified in Table 1:

TABLE 1 ingredients and concentrations as indicated by % of total weight

| ITEM | INGREDIENT (SUPPLIER/DISTRIBUTOR) | Percent (by wt.) |
|---|---|---|
| 1 | DIISOPROPYL ADIPATE | 21.800 |
| 2 | DIMETHICONE | 4.500 |
| 3 | HEPTYL UNDECYLENATE | 7.500 |
| 4 | COCONUT OIL | 3.000 |
| 5 | TIRETHYL CITRATE | 4.000 |
| 6 | BISABOLOL | 0.500 |
| 7 | WHITE BEESWAX | 9.500 |
| 8 | CARNAUBA WAX | 4.000 |
| 9 | SORBITAN OLEATE | 4.500 |
| 10 | GLYCERYL STEARATE | 3.500 |
| 11 | TAPIOCA | 1.000 |
| 12 | SODIUM BICARBONATE | 5.000 |
| 13 | ARROWROOT POWDER | 6.300 |
| 14 | ZEOLITE | 1.500 |
| 15 | DIMETHICONE | 5.000 |
| 16 | PURIFIED WATER | 0.500 |
| 17 | ALOE VERA | 0.100 |
| 18 | GLYCERIN | 12.000 |
| 19 | SODIUM BICARBONATE | 1.500 |
| 20 | ZINC CITRATE | 0.100 |
| 21 | SILVER CHLORIDE (JM ACTICARE P) | 0.200 |
| 22 | CORN STARCH | 4.000 |

Example 3

Exemplary embodiments of the invention include components of a deodorant formulation with the compositional characteristics identified in Table 2. The formula includes the following ingredients in the indicated concentrations as indicated by % of total weight:

TABLE 2

Ingredients and concentrations as indicated by % of total weight

| Ingredient | Narrow range | Broad range |
|---|---|---|
| Lipid Phase (includes Coconut Oil, silicones, Heptyl Undecylenate, waxes or esters) | 50%-60% | 35%-75% |
| Sorbitan Oleate (polyol fatty acid ester emulsifier) | 4%-6% | 2%-10% |

TABLE 2-continued

Ingredients and concentrations as indicated by % of total weight

| Ingredient | Narrow range | Broad range |
|---|---|---|
| Glyceryl Stearate (polyol fatty acid ester emulsifier) | 3%-5% | 1%-6% |
| Sodium Bicarbonate (in glycerin phase) | 0.5%-2.0% | 0.1%-5% |
| Sodium Bicarbonate (in lipid phase) | 3%-7% | 1%-15% |
| Maranta Arundinacea Root Powder | 5%-7% | 2%-10% |
| Zeolite | 1%-3% | 0.1%-5% |
| Glycerin | 10%-15% | 5%-25% |
| Corn Starch | 3%-5% | 1.5%-8.5% |
| Zinc Citrate | 0.001%-2% | 0.01%-0.5% |
| Silver Chloride, high amounts of silver are not practical for color stability, safety, and performance purposes. (Titanium Dioxide is part of Silver Chloride ingredient, not included for efficacy and % will be directly reflected by how much Silver is included). | 0.0002-0.006% | 0.0001%-0.1% |
| Triethyl Citrate | 3%-5% | 1%-10% |
| Bisabolol | 0.1%-1% | 0.05%-5% |
| Water | 0.2%-1% | 0.1%-2% |

Example 4

Examples of various components that can make up the agents of the invention in a deodorant formulation are identified in Table 3. The exemplary ingredients may be present alone or, preferably, in combination. The alternative ingredients may replace one or all of the exemplary ingredients in a particular formulation. This list is provided as an example and is not meant to be limiting.

TABLE 3 ingredients and alternatives

INGREDIENTS

| PURPOSE | EXEMPLARY INGREDIENTS | ALTERNATIVE INGREDIENTS |
|---|---|---|
| Odor Suppression | Sodium Bicarbonate Zeolites Magnesium Hydroxide | Citronella including partial extracts Sodium chloride Calcium chloride Magnesium sulfate |
| Anti-bacterial | Triethyl Citrate Any zinc (e.g. - zinc carbonate, zinc lactate, zinc citrate, zinc oxide, zinc ricinoleate) Silver Chloride and other silvers (e.g. silver carbonate, silver citrate) Zeolites | Witch Hazel Extract O-Cymen-5-ol |
| Moisture Absorption | Arrowroot Powder Corn Starch Tapioca Starch Starch Rice Starch Quinoa Starch Zeolites Clays (Fuller's earth clay, white clay, kaolin clay or another clay) Bamboo extract or other wood fiber extracts or powders | Silicone powder Silver Ear Mushroom extract Hyaluronic Acid Squalene Zinc Oxide |
| Skin Care | Bisapolol Calendula Extract Aloe Vera Coconut oil Vitamin E Arnica Extract | Maca Root Extract German and/or Roman Chamomile Jojoba Esters |

TABLE 3-continued ingredients and alternatives

INGREDIENTS

| PURPOSE | EXEMPLARY INGREDIENTS | ALTERNATIVE INGREDIENTS |
|---|---|---|
| Texture | Dimethicone Glycerin Beeswax Heptyl Undecylenate Sorbitan Stearate Copernica Cerifera (Carnauba) Wax Glyceryl Stearate Tapioca Starch Propanediol (or similar) Sorbitan isostearate Glyceryl oleate Sorbitan oleate Glyceryl laurate Glycol stearate Polyglyceryl-4 isostearate Polyglyceryl oleate Polyglyceryl-2 sesquiisostearate Polyglyceryl-2 diisostearate Helianthus Annuus (Sunflower) Oil Rosehip Seed Oil Theobroma Cacao (Cocoa) Seed Butter Castor (*Ricinus communis*) Oil Caprylic/Capric Triglyceride (fractionated coconut oil) Olea Europaea (Extra Virgin Olive Oil) Prunus Armeniacae (Apricot) Kernel Oil Shea Butter Sustainable (*Butyrospermum parkii*) Safflower Oil (*Carthamus tinctorius*), Cocoa Butter (*Theobroma cacao*) Palm Oil (*Elaecis oleifera*) Sweet Almond Oil (Prunus amygdalus dulcis) Jojoba Oil (*Simmondsia chinensis*) Avocado Oil (Persea Americana) Callophyllum inophyllum (tamanu) oil Euphorbia Cerifera (candelilla) Wax Dicapryl Carbonate Sorbitan Olivate Cetearyl Olivate Brassica Glycerides Xylityl Caprate/Caprylate | Glyceryl caprylate Glyceryl undecylenate Polyglyceryl-3 Caprate Other esters, powders and oils to achieve texture close to the benchmark |

Example 5

An exemplary embodiment of the invention is a deodorant formulation contains a fragrance and has the compositional characteristics identified in Table 4:

TABLE 4

Ingredients and concentrations as indicated by % of total weight

| ITEM | INGREDIENT (SUPPLIER/DISTRIBUTOR) | % |
|---|---|---|
| 1 | DIISOPROPYL ADIPATE | 21.300 |
| 2 | DIMETHICONE | 4.250 |
| 3 | HEPTYL UNDECYLENATE | 7.200 |
| 4 | COCONUT OIL | 2.700 |
| 5 | TRIETHYL CITRATE | 4.000 |

TABLE 4-continued

Ingredients and concentrations as indicated by % of total weight

| ITEM | INGREDIENT (SUPPLIER/DISTRIBUTOR) | % |
|---|---|---|
| 6 | BISABOLOL | 0.500 |
| 7 | WHITE BEESWAX | 9.500 |
| 8 | CARNAUBA WAX | 4.000 |
| 9 | SORBITAN OLEATE | 4.500 |
| 10 | GLYCERYL STEARATE | 3.500 |
| 11 | TAPIOCA PURE | 1.000 |
| 12 | SODIUM BICARBONATE | 5.000 |
| 13 | ARROWROOT POWDER | 6.300 |
| 14 | ZEOLITE | 1.500 |
| 15 | DIMETHICONE | 4.850 |
| 16 | PURIFIED WATER | 0.500 |
| 17 | ALOE VERA | 0.100 |
| 18 | GLYCERIN | 12.000 |
| 19 | SODIUM BICARBONATE | 1.500 |
| 20 | ZINC CITRATE | 0.100 |
| 21 | SILVER CHLORIDE (JM ACTICARE P) | 0.200 |
| 22 | CORN STARCH | 4.000 |
| 23 | FRAGRANCE ("THE VISIONARY") | 1.500 |

Fragrance ("The Visionary") is a mixture of Caprylic/Capric Triglyceride, Citrus Nobilis Peel Oil Expressed, Linalool, Lavandula Angustifolia (Lavender) Oil, Pelargonium Graveolens Flower Oil, Elettaria Cardamomum Seed Oil, and Dimethyl Heptenal.

A product review survey on an embodiment of the invention was conducted on a set of subjects. The age demographics of the subjects was:

25-34 years: 12 users;
34-44 years: 38 users;
45-54 years: 10 users;
65-74 years: 3 users.

Users provided the following information with respect to current product usage:

Currently using an aluminum-based antiperspirant: 42 users

Currently using a non-aluminum or natural deodorant: 21 users

Several users reported using more than one product.

The survey results are presented in Table 5 below.

TABLE 5

Results of comparative testing survey

| Question | Better | Same | Worse | Average Response |
|---|---|---|---|---|
| Q1 Overall, how did you enjoy using this deodorant? scale of 1 (didn't like at all) to 5 (loved it)* | 47 | 15 | 1 | 4.1 |
| Q2 How satisfied are you with your current product?* | 38 | 21 | 4 | 3.7 |
| Q3 How much did you enjoy using this new natural deodorant as compared to your current product? | 33 | 18 | 12 | — |
| Q4 How was this deodorant's odor protection as compared to your current product? | 17 | 26 | 20 | — |
| Q5 How was this deodorant's wetness protection as compared to your current product? | 9 | 30 | 24 | — |
| Q6 How does this sample compare to your experience with Tom's of Maine ®? | 17 | 3 | 0 | — |
| Q7 How does this sample compare to your experience with Schmidt's? | 5 | 1 | 0 | — |
| Q8 How does this sample compare to your experience with Native ®? | 4 | 0 | 0 | — |

*For Q1 and Q2, "Better" Combines responses of 4 and 5 (loved/liked), and "Worse" combines responses of 1 and 2 (didn't like)

TABLE 4

Results for Natural Users only

| Question | Better | Same | Worse | Average Response |
|---|---|---|---|---|
| Q1 Overall, how did you enjoy using this deodorant? scale of 1 (didn't like at all) to 5 (loved it)* | 17 | 4 | — | 4.3 |
| Q2 How satisfied are you with your current product?* | 10 | 8 | 1 | 3.7 |
| Q3 How much did you enjoy using this new natural deodorant as compared to your current product? | 14 | 4 | 3 | — |

TABLE 4-continued

Results for Natural Users only

| Question | Response (as compared to current or specific product) (number of users) | | | Average Response |
|---|---|---|---|---|
| | Better | Same | Worse | |
| Q4 How was this deodorant's odor protection as compared to your current product? | 9 | 9 | 3 | — |
| Q5 How was this deodorant's wetness protection as compared to your current product? | 5 | 11 | 5 | — |
| Q6 How does this sample compare to your experience with Tom's of Maine ®? | 1 | 1 | — | — |
| Q7 How does this sample compare to your experience with Schmidt's? | 1 | 1 | — | — |
| Q8 How does this sample compare to your experience with Native ®? | 2 | — | — | — |

Q9: How likely would you be to switch to this deodorant when it's available?
 (5) "absolutely, can't wait!": 18 users;
 (4): 19 users;
 (3): 19 users;
 (2): 5 users;
 (1) "it's not for me": 2 users
Natural Users Only:
Q9: How likely would you be to switch to this deodorant when it's available?
 (5) "absolutely, can't wait!": 7 users;
 (4): 7 users;
 (3): 7 users;
 (2): 0 users;
 (1) "it's not for me": 0 users It should be understood that various alternatives to the embodiments of the invention described herein may be employed in practicing the invention. It is intended that the scope of the invention, methods and structures within the scope of the invention includes equivalents.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A glycerin-in-oil deodorant composition comprising:
 a continuous phase comprising one or more oils, silicones, esters and/or waxes;
 a discontinuous phase comprising glycerin and water;
 an antimicrobial agent;
 a moisture-absorption agent;
 an odor neutralizing agent; and
 an emulsifier,
 wherein said one or more oils comprise triethyl citrate,
 wherein said antimicrobial agent comprises zinc citrate,
 wherein said moisture-absorption agent comprises arrowroot powder,
 wherein said odor neutralizing agent comprises sodium bicarbonate, and
 wherein said emulsifier comprises sorbitan oleate.

2. The glycerin-in-oil deodorant composition of claim 1, wherein the continuous phase comprises one or more of an oil, a silicone, heptyl undecylenate, and a wax.

3. The glycerin-in-oil deodorant composition of claim 2, wherein the oil, silicone, heptyl undecylenate, and/or wax together comprise from about 35% to about 75% by weight of the entire composition.

4. The glycerin-in-oil deodorant composition of claim 1, wherein the glycerin comprises from about 5% to about 25% by weight of the entire composition.

5. The glycerin-in-oil deodorant composition of claim 1, wherein the water comprises from about 0.1% to about 2% by weight of the entire composition.

6. The glycerin-in-oil deodorant composition of claim 1, wherein:
 the oil, silicone, and/or wax together comprise from about 35% to about 75% by weight of the entire composition;
 glycerin is present in an amount of from about 5% to about 25% by weight of the entire composition and the water is present in an amount of from about 0.1% to about 2% by weight of the entire composition;
 the antimicrobial agent comprises from about 1% to about 11% by weight of the entire composition;
 the moisture-absorption agent comprises from about 1% to about 30% by weight of the entire composition;
 the odor neutralizing agent comprises from about 0.1% to about 20% by weight of the entire composition; and
 the emulsifier comprises from about 1% to about 16% by weight of the entire composition.

7. The glycerin-in-oil deodorant composition of claim 1, wherein:
 the oil, silicone, and/or wax together comprise from about 50% to about 60% by weight of the entire composition;
 glycerin is present in an amount of from about 10% to about 15% by weight of the entire composition and the water is present in an amount of from about 0.2% to about 1% by weight of the entire composition;
 the antimicrobial agent comprises from about 3% to about 8% by weight of the entire composition;
 the moisture-absorption agent comprises from about 3% to about 18% by weight of the entire composition;
 the odor neutralizing agent comprises from about 3% to about 9% by weight of the entire composition; and the emulsifier comprises from about 7% to about 11% by weight of the entire composition.

8. The glycerin-in-oil deodorant composition of claim 1, further comprising at least one antimicrobial agent selected from the group consisting of silver chloride, triethyl citrate, witch hazel extract, zeolite, anti-microbial essential oils, zinc ricinoleate, and anti-microbial zinc salts.

9. The glycerin-in-oil deodorant composition of claim 1, wherein the antimicrobial agent comprises zinc citrate, silver chloride, and triethyl citrate.

10. The glycerin-in-oil deodorant composition of claim 1, further comprising at least one odor neutralizing agent selected from the group consisting of magnesium hydroxide, magnesium sulfate, zeolite, and citronella.

11. The glycerin-in-oil deodorant composition of claim 1, wherein the odor neutralizing agent comprises sodium bicarbonate in an amount of from about 0.1% to about 20% by weight of the entire composition.

12. The glycerin-in-oil deodorant composition of claim 1, further comprising at least one moisture-absorption agent selected from the group consisting of corn starch, tapioca starch, potato starch, zeolite, rice starch, silicone powder, clay, silver ear mushroom extract, hyaluronic acid, squalene, zinc oxide, and silver.

13. The glycerin-in-oil deodorant composition of claim 1, wherein the moisture-absorption agent from about 0.1% to about 10% by weight of the entire composition.

14. The glycerin-in-oil deodorant composition of claim 13, wherein the moisture-absorbing agent further comprises one or more of tapioca, and corn starch.

15. The glycerin-in-oil deodorant composition of claim 1, wherein the emulsifier has a hydrophilic-lipophilic balance of between 1 and 8.

16. The glycerin-in-oil deodorant composition of claim 1, wherein the emulsifier is present in an amount of from about 1% to about 16% by weight of the entire composition.

17. The glycerin-in-oil deodorant composition of claim 1, comprising one or more of diidopropyl adipate, dimethicone, heptyl undecylenate, coconut oil, bisabolol, bees wax, carnauba wax, tapioca starch, maranta arundinacea root powder, a zeolite, corn starch, aloe vera gel, and titanium dioxide.

18. The glycerin-in-oil deodorant composition of claim 1, wherein the composition is essentially free of aluminum salts and zirconium salts.

19. A method for treating perspiration in a subject comprising contacting a skin surface region of the subject with the compositions of claim 1.

20. A glycerin-in-oil deodorant composition comprising:
a continuous phase comprising one or more oils, silicones and/or waxes;
a discontinuous phase comprising glycerin and water;
an antimicrobial agent comprising zinc citrate, and silver chloride;
an odor neutralizing agent comprising sodium bicarbonate, wherein the sodium bicarbonate is present in the continuous phase and in the discontinuous phase;
a moisture-absorption agent comprising a hydrophilic starch; and
an emulsifier,
wherein said one or more oils comprise triethyl citrate,
wherein said emulsifier is sorbitan oleate, and
wherein said odor neutralizing agent comprising sodium bicarbonate makes up from 3.0% to 10% by weight of the entire composition.

* * * * *